United States Patent [19]

Stauffer

[11] Patent Number: Plant 5,642

[45] Date of Patent: Jan. 21, 1986

[54] AVOCADO TREE

[76] Inventor: Royce D. Stauffer, 234 Toro Canyon Rd., Carpinteria, Calif. 93013

[21] Appl. No.: 633,973

[22] Filed: Jul. 24, 1984

[51] Int. Cl.[4] ..... A01H 5/03

[52] U.S. Cl. ..... Plt./44

[58] Field of Search ..... Plt./44

*Primary Examiner*—Robert E. Bagwill

[57] ABSTRACT

A new avocado variety developed from a seedling tree is recommended for clonal rootstock, The tree has a history of survival under adverse soil conditions and good tank test resistance to *Phytophthora cinnamomi.* Field tests show some superiority to presently used clonal rootstocks.

2 Drawing Figures

1

This invention relates to a new and distinct variety of avocado tree useful as clonal rootstock. This variety has been named Toro Canyon.

The upper photograph illustrates the appearance of the tree in January with many blossoms and some juvenile fruit. Mature leaves and the underside of a mature leaf are also shown. The lower photograph illustrates the appearance of the tree in July with bronze new growth and almost mature fruit. Both sides of a mature leaf are shown.

ORIGIN

The inventor owns property on Toro Canyon Road near Carpinteria, Calif. that is unsuitable for avocado prouction. The soil is Milpitas-Positas fine sandy loam underlain at 18" with dense very slowly permeable clay subsoil. Successive plantings of commercial nursery trees have failed 100% with root rot. Approximately 20 seeds were planted on this property. The subject avocado tree is one of three 18-year survivors. The seed came from a Topa-Topa seedling which had been planted for rootstock purposes. Rincon, Dickinson, MacArthur and Hass wer available as pollenizers. The tree, which is quite unlike Topa-Topa, is possibly a hybrid with Rincon. The crushed foliage has only a moderate anise odor.

Asexual Reproduction

The parent tree which was grafted to Hass grew several shoots from the roots. Three trees were grown by dividing off these shoots. Brokaw Nursery, Inc., with the permission of the applicant, has since reproduced this tree more efficiently (U.S. Pat. No. 4,012,866), both alone and with a Hass top.

The Tree

The tree is a vigorous grower with short internodes, dense foliation and a spread somewhat exceeding its height. Suitably maintained trees develop a caliper over 5 cm 14 months after transplanting from the nursery. The mature bark is prominently lenticeled giving the appearance of uniform horizontal dashes. On a trunk 8 cm in diameter these lenticels are about 5 mm long, 1 mm high and distinctly protrude above the bark surface.

2

Foliage

The leaf blade is oval pointed in shape. The top surface is a dark green (Dictionary of Color, Maerz and Paul, 2nd Ed., Plate 23, L, 8-9), smooth and with a slight gloss. The underside is of a gray-green (Plate 21, E-G, 6), dull and pubescent. The edge is smooth and undulant. Mature leaves average about 15 cm long and 7 cm wide. The new growth is bronze fading rapidly to green as the leaf matures. The amount of bronze displayed is somewhat less than Pinkerton (U.S. Plant Pat. No. 3,712) and much less than Hass. Leaves on Brokaw-reproduced clones grown on Yolo loam near Fillmore, Calif. are indistinguishable from leaves of the parent tree near Carpinteria in either size or color.

Fruit

Typical fruit is pyriform in shape, 11 cm long and weighs 185 g. The skin is thin and smooth. The color is green flecked with yellow becoming purple at maturity. In Carpinteria most fruit matures in August although fruits in other stages of development are also on the tree. The seed is loose in the cavity and the seed coat tends to stick to the fruit when cut. The flesh does not soften uniformly, contains considerable fiber which blackens upon softening, and tastes inferior to commercial avocados.

Rootstock Potential

Hass tops established on rootstock of this tree are vigorous and productive. This tree, by its origin, has shown unusual ability to survive under adverse soil conditions. Rooted cuttings were tank tested for resistance to *Phytophthora cinnamomi* at the University of California. This test demonstrated resistance similar to the best known clonal rootstocks. Field tests in comparison with other clonal rootstocks are in progress. It is believed that the subject rootstock has shown superiority over currently used clonal rootstocks.

I claim:

1. A new and distinct variety of avocado tree as herein disclosed, characterized by vigorous growth, both alone and with a Hass top, and an unusual ability to survive under adverse soil conditions as shown by its origin and subsequent tests.

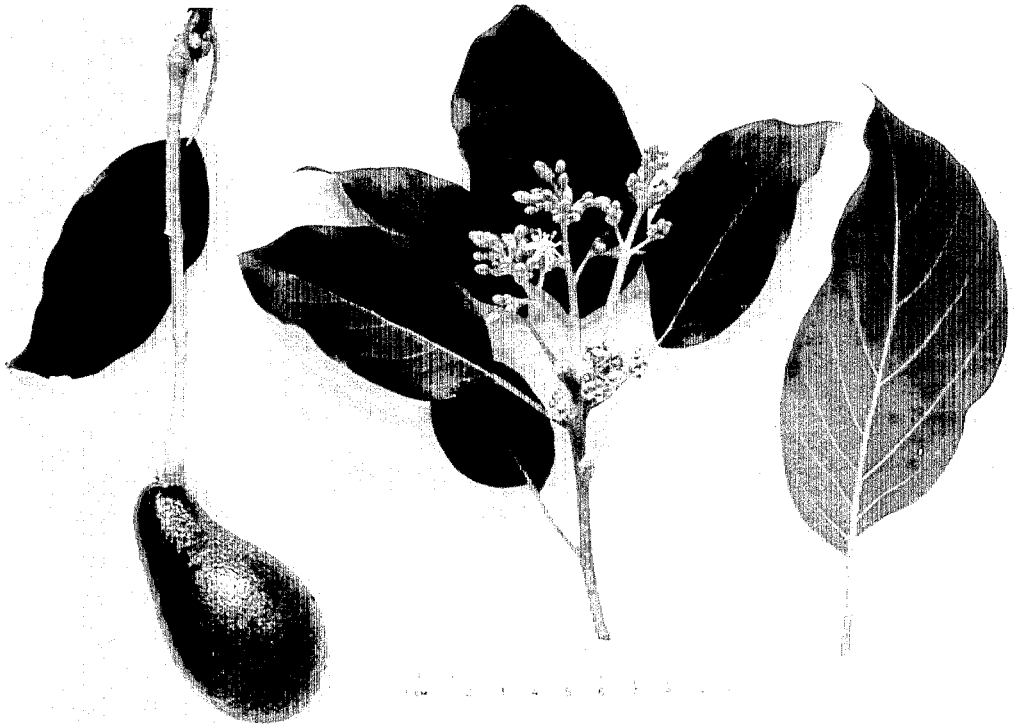
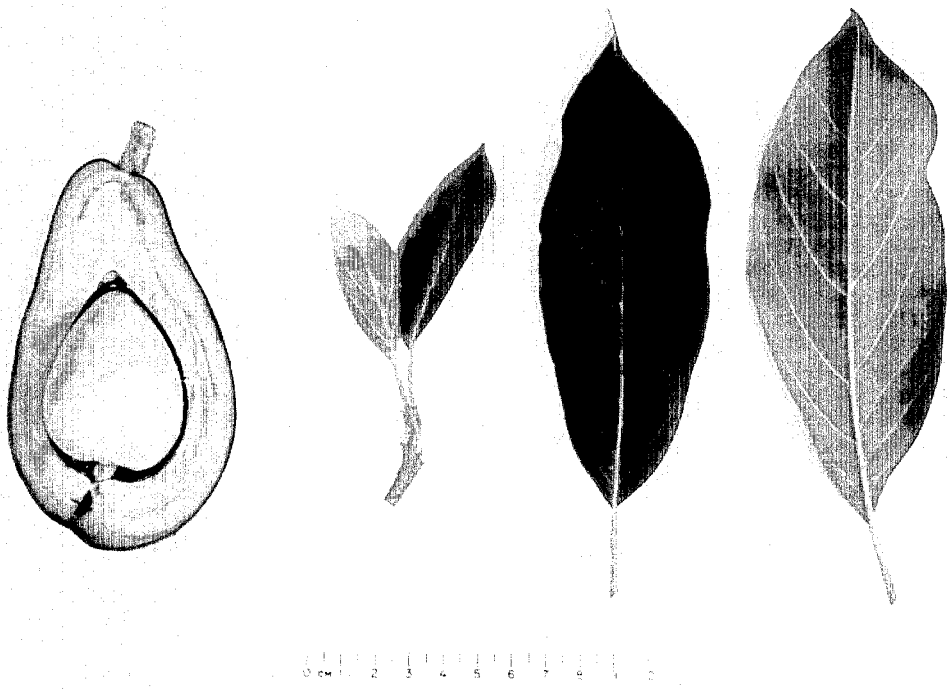

* * * * *